United States Patent [19]

Lay et al.

[11] Patent Number: 4,489,058
[45] Date of Patent: Dec. 18, 1984

[54] ACNE CONTROL METHOD

[75] Inventors: George E. Lay, Fountaintown, Ind.; Daniel H. Haigh, Sanford, Mich.; Richard A. Knipstein, Carmel, Ind.

[73] Assignee: The Dow Chemical Company, Midland, Mich.

[21] Appl. No.: 497,296

[22] Filed: May 23, 1983

[51] Int. Cl.³ .................. A61K 31/74; A61K 31/78; A61K 31/745

[52] U.S. Cl. ........................ 424/78; 424/81; 424/83

[58] Field of Search .............. 424/81, 78, 83

[56] References Cited

U.S. PATENT DOCUMENTS

| 3,520,806 | 7/1970 | Haigh | 210/40 |
| 3,615,972 | 10/1971 | Morehouse et al. | 156/79 |
| 3,697,643 | 10/1972 | Shepherd | 424/63 |
| 3,849,576 | 11/1974 | Kalopissis | 424/330 |
| 4,039,489 | 8/1977 | Fletcher et al. | 260/2.5 AP |
| 4,071,670 | 1/1978 | Vanzo et al. | 526/88 |
| 4,112,067 | 9/1978 | Tomalia et al. | 424/78 |
| 4,186,191 | 1/1980 | Chamberlin et al. | 424/78 |
| 4,356,190 | 10/1982 | Kraskin | 424/319 |
| 4,364,940 | 12/1982 | Neiss et al. | 424/230 |
| 4,367,227 | 1/1983 | Bingham | 424/243 |

OTHER PUBLICATIONS

Elastomers, Ed. 2, A Desk Top Data Bank, Pub. The International Plastics Selector, Inc., pp. 197, 198 & 902, (1980).

*Primary Examiner*—Leonard Schenkman

[57] ABSTRACT

A method for controlling acne or acneform eruptions in humans is disclosed. The method involves the topical application of one or more sebum-imbibing, sebum-retaining polymers either alone or in combination with a pharmaceutically acceptable carrier.

19 Claims, No Drawings

ACNE CONTROL METHOD

BACKGROUND OF THE INVENTION

The incidence of acne in the adolescent is nearly universal. In response to an increased production of androgenic hormones during puberty, the sebaceous glands produce greater amounts of sebum with a consequent increase in the oily characteristic of the skin. The sebaceous glands, which are located in the dermis, possess a duct opening into the individual hair follicles thereby providing a means for the sebum to reach the surface of the skin. The sebum secreted by the sebaceous glands is a mixture of fats and waxes and serves to maintain a proper degree of hydration to the hair and skin. However, in the presence of normal epithelial bacteria, notably *Corynebacterium acnes*, the triglycerides present in the sebum are enzymatically split into free fatty acids which initiate a primary follicular inflammation (i.e., acne). Because of the role that sebum plays in the etiology of acne, preventive measures are primarily concerned with reduction in the quantity of sebum present on the skin and underlying tissue. Thus, it would be desirable to provide a means whereby excessive amounts of sebum could be effectively removed from the skin surface and underlying tissue thereby reducing the quantity of triglycerides available for lipolysis into free fatty acids consequently preventing the initiation of acne or acneform eruptions.

SUMMARY OF THE INVENTION

The present invention is directed to a method of controlling acne or acneform eruptions in humans caused wholly or partially by the excessive production and secretion of sebum onto the skin. The method comprises the topical application of an effective amount of one or more uncrosslinked or lightly crosslinked polymers capable of imbibing and retaining sebum when contacted therewith on the surface of the skin.

The pharmaceutically acceptable sebum-imbibing, sebum-retaining polymers employed in the method of the present invention are homopolymers of aliphatic diolefins (i.e. alkadienes) or copolymers having polymerized therein two or three monomer units selected from the group consisting of alkenyl aromatic compounds; alkyl esters derived from an aliphatic alcohol and acrylic or methacrylic acid; vinyl esters of aliphatic carboxylic acids; and aliphatic diolefins.

The alkenyl aromatic compounds which may be utilized in the preparation of the polymers useful for the method described herein contain a straight or branched chain alkenyl residue of from 2 to about 10 carbon atoms and may optionally be ring substituted with halogen or a straight or branched chain alkyl moiety of from 1 to about 20 carbon atoms. Such compounds include, for example, various halostyrenes such as 2-chlorostyrene, 3-fluorostyrene, 4-fluorostyrene and the like; vinyl naphthalenes, allylbenzene, 2-phenyl-2-butene, styrene and various substituted styrenes such as alkylstyrenes. Such alkylstyrenes include, for example, n-alkylstyrenes such as methylstyrene (i.e., vinyl toluene), n-butylstyrene, n-amylstyrene, n-octylstyrene, n-octadecylstyrene and the like; isoalkylstyrenes such as isobutylstyrene, isohexylstyrene, isododecylstyrene and the like; sec-alkylstyrenes such as sec-butylstyrene, sec-hexylstyrene, sec-octylstyrene and the like; tertiary-alkylstyrenes such as tert-butylstyrene, tert-amylstyrene, tert-octylstyrene, tert-eicosylstyrene and the like.

The alkyl esters derived from an aliphatic alcohol and acrylic or methacrylic acid useful in the method of the present invention are acrylate or methacrylate esters derived from an alcohol moiety containing from 1 to about 20 carbon atoms. Such esters include, for example, butyl methacrylate, butyl acrylate, hexyl acrylate, isobornyl methacrylate, cetyl methacrylate, eicosyl acrylate, the mixed ester cetyl-eicosyl methacrylate, lauryl methacrylate, stearyl methacrylate, isobornyl acrylate, and lauryl acrylate.

The vinyl esters of aliphatic carboxylic acids used in the preparation of the polymers utilized in the method described herein are esters prepared from carboxylic acids containing from 2 to about 20 carbon atoms such as vinyl acetate, vinyl butyrate, vinyl stearate, vinyl 2-ethylhexoate and the like.

The aliphatic diolefins used in the preparation of the polymers described herein are alkadienes containing from about 4 to about 12 carbon atoms such as butadiene, pentadiene, 2-methyl-1,3-butadiene and the like.

Of the alkenyl aromatic compounds previously described, those preferred for preparation of the polymers used in the present invention are styrene and ring-substituted styrene wherein said substituent is a straight or branched chain alkyl moiety of from one to about twelve carbon atoms (alternatively referred to as an alkylstyrene) such as vinyl toluene, n-hexylstyrene, sec-octylstyrene, tert-butylstyrene, n-dodecylstyrene and the like. Relative to the alkyl esters derived from a $C_1$ to $C_{20}$ alcohol and acrylic or methacrylic acid, those which are preferred are acrylate or methacrylate esters derived from an alcohol moiety containing from about 8 to about 20 carbon atoms, and may be a linear fatty alcohol residue such as cetyl, lauryl, stearyl, or eicosyl, or a secondary alcohol residue. Of the vinyl esters of aliphatic carboxylic acids, those preferred for use in the method of the present invention are those wherein the aliphatic carboxylic acid contains from about 8 to about 20 carbon atoms such as vinyl stearate. Of the aliphatic diolefins, those diolefins containing from 4 to about 6 carbon atoms are preferred.

Preferred polymers suitable for use in the method of the present invention are uncrosslinked or lightly crosslinked polymers of styrene or alkylstyrene (wherein said alkyl moiety may be a straight or branched chain alkyl moiety of from 1 to about 12 carbon atoms) and one or two comonomers selected from the group consisting of (a) an alkyl ester of a $C_1$ to $C_{20}$ alcohol and acrylic or methacrylic acid; (b) a vinyl ester of a $C_8$ to $C_{20}$ carboxylic acid; or (c) an aliphatic diolefin of from about 4 to about 6 carbon atoms. The alkylstyrene can be, for example, vinyl toluene or preferably a tertiary-alkylstyrene such as 4-tert-butylstyrene, 4-tert-amylstyrene, 3,5-ditert-butylstyrene, 4-tert-hexylstyrene, 4-tert-octylstyrene and the like. The alkyl ester monomer preferably though not necessarily includes one or both of a methacrylate or acrylate ester of one or more $C_8$ to about $C_{20}$ fatty alcohols, or a $C_{10}$ to about $C_{20}$ fatty alcohol methacrylate or acrylate as essentially the sole comonomer. The vinyl ester may be an ester of a $C_8$ to $C_{20}$ carboxylic acid such as vinyl stearate, vinyl palmitate, vinyl laurate and the like. The aliphatic diolefin is preferably butadiene. Such polymers may contain from about 5 to about 95 percent styrene or alkylstyrene monomer by weight. Preferably, the polymer may contain from about 30 to about 60 to about 85 to about 90 percent by weight of styrene or alkylstyrene.

Other preferred polymers useful in the method of the present invention are uncrosslinked or lightly crosslinked polymers prepared from alkyl ester monomers derived from a $C_8$ to $C_{20}$ alcohol and one or both of acrylic or methacrylic acid; uncrosslinked or lightly crosslinked polymers prepared from an alkyl ester derived from a $C_8$ to $C_{20}$ alcohol and acrylic or methacrylic acid as a comonomer with a vinyl ester of an aliphatic carboxylic acid containing from about 8 to about 20 carbon atoms, said polymer containing from about 20 to about 70 percent by weight of the vinyl ester. Also preferred are homopolymers of aliphatic diolefins containing from about 4 to about 6 carbon atoms, such as polybutadiene.

Of the preferred polymers described above, those which are particularly preferred for use herein are uncrosslinked or lightly crosslinked polymers of styrene and lauryl methacrylate; vinyl toluene and lauryl methacrylate; styrene and butadiene; polymers of tertiary-butylstyrene with lauryl methacrylate, stearyl methacrylate or vinyl stearate; terpolymers of tertiary-butylstyrene, 2-ethylhexyl acrylate and lauryl methacrylate; terpolymers of tertiary-butylstyrene, 2-ethylhexyl acrylate and stearyl methacrylate; polymers of isobornyl methacrylate and lauryl methacrylate; polymers of vinyl stearate and lauryl methacrylate or isobornyl methacrylate; and a homopolymer of butadiene (i.e., polybutadiene). Of the particularly preferred polymers, those which are most particularly preferred are those substantially as described in Table 1, below.

The polymer utilized herein may be uncrosslinked or lightly crosslinked with a minor amount of a crosslinking agent. In those instances where the polymer utilized is uncrosslinked, it will exhibit a film-like consistency owing to the solubility of the polymer in the sebum present on the skin. When lightly crosslinked as described herein, the polymers will be insoluble in and immiscible with the sebum. In either instance, the polymer used retains its sebum-imbibing, sebum-retaining character. Excessive crosslinking may hinder or prevent the polymeric particles from imbibing the sebum from the skin surface. In general, the polymers can contain from about 0.001 to about 2 percent by weight of a crosslinking agent (based on total weight of the polymer). Preferably, about 0.01 to about 0.05 to about 0.075 percent of crosslinking agent is employed. The crosslinking agent can be any di- or poly-functional compound known to be useful as a crosslinking agent such as divinylbenzene, vinyl isopropenyl benzene, or other polyethylenically unsaturated crosslinking agents described, for example, in U.S. Pat. No. 3,520,806. Divinylbenzene is preferred as a crosslinking agent, in amounts from about 0.01 to about 0.05 to about 0.075 to about 0.1 weight percent.

The particle size diameter of the polymers utilized herein may vary based on considerations such as desired rate of sebum absorption, the particular pharmaceutical composition for topical application and the like. For instance, for a given amount of polymer applied, the contact with the sebum and the subsequent rate of sebum absorption is generally enhanced as the ratio of surface area to weight of the polymer increases. In general, for the method described herein, the particles may be from about 100 Angstrom units to about 2 millimeters (mm) wide at their smallest diameter. It is convenient and preferred to employ generally spherical particles with diameters of from about 50 to about 500 microns.

The small particles may be prepared by a variety of known methods such as grinding, milling, cutting or comminuting extruded strands of polymer, or by emulsion or suspension polymerization techniques. Various suitable techniques are disclosed in U.S. Pat. Nos. 3,615,972 and 4,071,670. Suspension polymerization is a well-known process for forming polymer particles with spherical or bead-like configurations and relatively uniform particle size, and this technique can be conveniently employed to make the polymers.

The polymers utilized by the method described herein are either commercially available or are prepared by well-known techniques. For example, the polymers may be prepared by emulsion or suspension polymerization of the monomers (and crosslinking agent) in an aqueous emulsion or aqueous suspension. In emulsion polymerization, the polymerization occurs in micelles formed by the monomer mixture and the emulsifier. In the suspension technique, polymerization occurs in monomer droplets suspended in the aqueous phase. Suspension polymerization is preferred for making larger particles, e.g., from about 0.3 to about 0.5 micron and larger.

The polymerization reaction proceeds at temperatures from about 50° to about 120° C., conveniently from 70° to 90° C., and in the presence of a minor amount (typically from about 0.5 to about 10 times the amount of the crosslinking agent) of a polymerization initiator such as potassium persulfate or tertiary-butyl peroctoate. In preparing the polymers, the monomers and crosslinking agent are mixed together in the proportions corresponding to those desired for the product, then dispersed in water containing either an emulsifying agent or a suspending agent. The proportions are preferably selected so the monomer plus crosslinking agent comprise about 20 to about 60 percent by weight of the aqueous mixture. The polymerization initiator is mixed with either the monomer mixture or the aqueous phase depending on the polymerization method, the initiator used and its relative solubility in the two phases. The mixture is then mixed in order to disperse the monomer phase in the aqueous phase, and to reduce the particle size of the mixture of monomer and crosslinking agent to the size desired for suspension polymerization; and to form micelles of the desired size for emulsion polymerization. The resulting mixture is heated with stirring at a temperature in the polymerization temperature range until the reaction is substantially complete (generally about 4 to about 24 hours). The polymer product can be recovered and worked up by conventional techniques such as filtration or screening to remove any coagulum or large-particle waste, dialysis, lyophilization or, particularly, with polymer particle sizes on the order of 0.15 micron and larger, by filtration to separate the reaction medium, alcohol precipitation, washing with lower alkanols, steam distillation or other known techniques.

In a convenient purification procedure for polymer particles prepared by suspension polymerization, the suspension is passed through a screen to remove all large coagulum waste particles, then mixed with about 10 parts by volume of isopropanol. The particles are allowed to settle, and the supernatant liquid removed by decantation. Washing with isopropanol can be repeated, if desired. The washed polymer particles can be separated by conventional techniques such as decantation, centrifugation, evaporation, or filtration. The washed particles can be used directly or suspended in an aqueous carrier.

Purification is preferably achieved by isolating the material as a filter cake and then sequentially washing the intact filter cake with deionized water and then an alcohol such as, for example, 95 percent ethanol or isopropanol, under pressure.

In practicing the method of the present invention, an effective amount of one or more of the polymers described herein or a pharmaceutically acceptable composition thereof is applied topically to the skin where control of acne or acneform eruptions is desired. As used herein, the term "effective amount" refers to that amount of one or more polymers described herein sufficient to cause a decrease in the amount of sebum present on the skin, wherein such decrease will lead to the control of acne or acneform eruptions in subjects in need of such treatment. As used herein, the phrase "control of acne or acneform eruptions" refers to the prevention of, or reduction in the severity of said acne or acneform eruptions caused wholly or partially by the excessive production and secretion of sebum onto the surface of the skin. The polymers or compositions thereof can be applied in any pharmaceutically acceptable form, that is, in any physical form in which the polymer can be conveniently contacted with the affected area of the skin, but which does not cause significant irritation of the skin. Preferably, the polymers described herein are employed in the form of small particles, such as granules, powders, beads, or small spherical particles (see, e.g., U.S. Pat. No. 3,615,972) in combination with a pharmaceutically acceptable carrier in suitable form for topical application. The polymers described herein may also, when present in an appropriate solvent system, be incorporated into pharmaceutical compositions suitable for topical application. Such compositions exhibit a film-like characteristic upon drying which conveniently facilitates removal of the composition containing the polymer and the sebum imbibed therein. The above-described compositions may additionally contain any physiologically beneficial ingredients, excipients, adjuvants, perfumes, thickeners, stabilizers, and the like. Methods for preparing the pharmaceutically acceptable compositions described herein for use in the present invention are well-known to the art. See, for example, *Remington's Pharmaceutical Sciences*, pp. 1461–1762, 14th Edition (Mack Publishing Company, 1970), which is incorporated herein by reference. In general, compositions containing the polymers described herein may contain from about 5 to about 50 percent by weight of one or more polymers. Higher concentrations are also operable, but may be less aesthetically pleasing above the given range.

DETAILED DESCRIPTION OF THE INVENTION

The following examples are set forth as a means of illustrating the present invention and are not to be construed as a limitation thereon.

EXAMPLE 1

The polymers described in Table 1 were prepared by techniques well-known to the art or were commercially obtained and then tested according to the method described in Example 2.

TABLE 1

| Polymer No. | Polymer Composition* | | | | | Divinyl benzene** (Percent by Weight) |
|---|---|---|---|---|---|---|
| | % $M_1$ | | % $M_2$ | | % $M_3$ | |
| 1 | 70 | IBoMA | 30 | VS | | 0.075 |
| 2 | 50 | IBoMA | 50 | LMA | | 0.075 |
| 3 | 55 | IBoMA | 45 | LMA | | 0.075 |
| 4 | 50 | VS | 50 | LMA | | 0.05 |
| 5 | 70 | VT | 30 | LMA | | 0.075 |
| 6 | 60 | STY | 40 | LMA | | 0.05 |
| 7 | 70 | STY | 30 | LMA | | 0.075 |
| 8 | 64 | tBS | 36 | LMA | | 0.05 |
| 9 | 65 | tBS | 35 | LMA | | 0.05 |
| 10 | 70 | tBS | 30 | LMA | | 0.05 |
| 11 | 70 | tBS | 30 | VS | | 0.075 |
| 12 | 50 | tBS | 50 | SMA | | 0.05 |
| 13 | 60 | tBS | 40 | SMA | | 0.05 |
| 14 | 65 | tBS | 35 | SMA | | 0.0125 |
| 15 | 65 | tBS | 35 | SMA | | 0.025 |
| 16 | 65 | tBS | 35 | SMA | | 0.05 |
| 17 | 65 | tBS | 35 | SMA | | 0.10 |
| 18 | 67.5 | tBS | 32.5 | SMA | | 0.05 |
| 19 | 70 | tBS | 30 | SMA | | 0.05 |
| 20 | 75 | tBS | 25 | SMA | | 0.05 |
| 21 | 80 | tBS | 20 | SMA | | 0.05 |
| 22 | 70 | tBS | 20 | EHA | 10 LMA | 0.05 |
| 23 | 70 | tBS | 20 | EHA | 10 SMA | 0.05 |
| 24 | 70 | BUT | 30 | STY | | |
| 25 | 100 | PBD$^a$ | | | | |
| 26 | 100 | PBD$^b$ | | | | |

*Percent by weight of each comonomer ($M_1$, $M_2$ and $M_3$) having the following designations:
IBoMA = Isobornyl methacrylate; VS = Vinyl stearate; LMA = Lauryl methacrylate;
VT = Vinyl toluene; STY = Styrene; tBS = tert-butylstyrene; SMA = Stearyl methacrylate;
EHA = 2-Ethylhexyl acrylate; BUT = Butadiene; PBD = Polybutadiene.
**Present as a crosslinking agent.
$^a$Diene 35 (A trademark of the Firestone Synthetic Rubber and Latex Co.)
$^b$Diene 55 (A trademark of the Firestone Synthetic Rubber and Latex Co.)

EXAMPLE 2

A composition simulating human sebum was prepared by admixing the following constituents in the stated proportions (percent by weight):

| | |
|---|---|
| Cholesterol | 2.5 |
| Oleic Acid | 25.0 |
| Triolein | 30.0 |
| Cetyl palmitate | 25.0 |
| Cholesterol oleate | 2.5 |
| Squalene | 15.0 |

In order to test the capacity of a given polymer to imbibe sebum, the following procedure was performed.

In a microscope well slide was placed one bead of the polymer to be tested having an initial bead diameter of from about 150 to about 450 microns. To this was added a quantity of the human sebum composition described above sufficient to cover the bead. The temperature was maintained at about 37° C. during the course of the experiment and bead diameter measurements were made microscopically at the initiation of the experiment and periodically throughout until the point of maximum imbibition of the sebum by the bead had been reached (usually about 95 to about 300 minutes from the start of the experiment). The bead diameter measurements were then utilized to ascertain the degree of imbibition of the sebum composition by the bead and are set forth in Table 2.

TABLE 2

| Polymer No. | Initial Bead Diameter (Microns) | Approximate Bead Diameters in Microns Measured At Various Time Intervals (in Minutes) | | | | | Percent Increase |
|---|---|---|---|---|---|---|---|
| | | 60 | 120 | 180 | 240 | Final | |
| 1 | 150 | 153 | 153 | — | — | 160 | 6.7 |
| 2 | 149 | 300 | 309 | 309 | — | 309 | 107.4 |
| 3 | 151 | 297 | 310 | — | — | 310 | 105.3 |
| 4 | 150 | — | — | — | — | 330 | 120.0 |
| 5 | 150 | 270 | 280 | 281 | — | 281 | 87.3 |
| 6 | 151 | 294 | — | — | 316 | 316 | 109.3 |
| 7 | 149 | 230 | — | — | 238 | 238 | 59.7 |
| 8 | 150 | 311 | 320 | 322 | — | 322 | 114.7 |
| 9 | 150 | 303 | 317 | 317 | — | 317 | 111.3 |
| 10 | 148 | — | — | — | — | 312 | 110.8 |
| 11 | 150 | 220 | 245 | 264 | 270 | 275 | 83.3 |
| 12 | 153 | 331 | — | — | — | 340 | 122.2 |
| 13 | 150 | — | — | — | 336 | 336 | 124.0 |
| 14 | 152 | — | — | 430 | 435 | 435 | 186.2 |
| 15 | 153 | — | — | — | — | 345 | — |
| 16 | 152 | — | — | — | — | 387 | 154.6 |
| 17 | 148 | — | — | — | — | 278 | 87.8 |
| 18 | 148 | 310 | — | — | — | 320 | 116.2 |
| 19 | 150 | 310 | — | — | — | 324 | 116.0 |
| 20 | 149 | 285 | 318 | — | — | 322 | 116.1 |
| 21 | 148 | 252 | — | — | — | 303 | 104.7 |
| 22 | 150 | 300 | 318 | — | 13 | 318 | 112.0 |
| 23 | 150 | — | — | — | — | 310 | 106.7 |
| 24 | 381 | 638 | 683 | — | — | 705 | 85.0 |
| 25 | 428 | 645 | 675 | — | — | 675 | 57.7 |
| 26 | 353 | 818 | 855 | — | — | 855 | 142.2 |

*From Table 1.
*Where no value is stated, a diameter measurement was not made at the time specified.
*Value represents the percent increase of the final bead diameter from the initial bead diameter.
i.e. $\frac{\text{Final Diameter} - \text{Initial Diameter}}{\text{Initial Diameter}} \times 100$ As can be seen from the data in Table 2, all of the polymers tested increased in diameter due to imbibition of the sebum composition. Significantly, all but seven of the polymers tested doubled in diameter from the initial bead diameter.

What is claimed is:

1. A method for controlling acne or acneform eruptions in humans which comprises the topical application of an effective amount of a crosslinked or uncrosslinked sebum-imbibing, sebum-retaining polymer, wherein the polymer is the polymerization product of two or three monomer units selected from the group consisting of styrene or alkylstyrene ring substituted with a straight or branched chain alkyl moiety of from 1 to about 12 carbon atoms; an alkyl ester derived from an alcohol containing from about 8 to about 20 carbon atoms and acrylic or methacrylic acid; a vinyl ester of an aliphatic carboxylic acid containing from about 8 to about 20 carbon atoms; and an aliphatic diolefin of from about 4 to about 6 carbon atoms.

2. A method for controlling acne or acneform eruptions in humans which comprises the topical application of an effective amount of a sebum-imbibing, sebum-retaining homopolymer of an aliphatic diolefin of from about 4 to about 6 carbon atoms.

3. The method of claim 1 wherein the polymer is a crosslinked polymer of from about 30 to about 90 percent by weight of styrene and an alkyl ester derived from an alcohol containing from about 8 to about 20 carbon atoms and acrylic or methacrylic acid, cross-linked with from about 0.001 to about 0.1 percent (based on total weight of said polymer) of a polyethylenically unsaturated crosslinking agent.

4. The method of claim 1 wherein the polymer is a crosslinked polymer of from about 30 to about 90 percent of styrene and an aliphatic diolefin of from about 4 to about 6 carbon atoms.

5. The method of claim 1 wherein the polymer is a crosslinked polymer of from about 30 to about 90 percent vinyl toluene and an alkyl ester derived from an alcohol containing from about 8 to about 20 carbon atoms and acrylic or methacrylic acid, crosslinked with from about 0.001 to about 0.1 percent (based on total weight of said polymer) of a polyethylenically unsaturated crosslinking agent.

6. The method of claim 1 wherein the polymer is a crosslinked polymer of alkyl ester monomers derived from an alcohol containing from about 8 to about 20 carbon atoms and acrylic or methacrylic acid, crosslinked with from about 0.001 to about 0.1 percent (based on total weight of said polymer) of a polyethylenically unsaturated crosslinking agent.

7. The method of claim 1 wherein the polymer is a crosslinked polymer of from about 20 to about 70 percent of a vinyl ester of an aliphatic carboxylic acid containing from about 8 to about 20 carbon atoms and an alkyl ester derived from an alcohol containing from about 8 to about 20 carbon atoms and acrylic or methacrylic acid, cross-linked with from about 0.001 to about 0.1 percent (based on total weight of said polymer) of a polyethylenically unsaturated crosslinking agent.

8. The method of claim 1 wherein the polymer is a crosslinked polymer of from about 30 to about 90 percent of a tertiary-alkylstyrene containing from about 4 to about 12 carbon atoms and at least one alkyl ester derived from an alcohol containing from about 8 to about 20 carbon atoms and acrylic or methacrylic acid, crosslinked with from about 0.001 to about 0.1 percent (based on the total weight of said polymer) of a polyethylenically unsaturated crosslinking agent.

9. The method of claim 1 wherein the polymer is a crosslinked polymer of from about 30 to about 90 percent of a tertiary-alkylstyrene containing from about 4 to about 12 carbon atoms and a vinyl ester of an aliphatic carboxylic acid containing from about 8 to about 20 carbon atoms, crosslinked with from about 0.001 to about 0.1 percent (based on the total weight of said polymer) of a polyethylenically unsaturated crosslinking agent.

10. The method of claim 2 wherein the homopolymer is polybutadiene.

11. The method of claim 3 wherein the alkyl ester is lauryl methacrylate and the crosslinking agent is divinylbenzene.

12. The method of claim 4 wherein said aliphatic diolefin is butadiene.

13. The method of claim 5 wherein said alkyl ester is lauryl methacrylate and the crosslinking agent is divinylbenzene.

14. The method of claim 6 wherein said alkyl ester monomers are isobornyl methacrylate and lauryl methacrylate and the crosslinking agent is divinylbenzene.

15. The method of claim 7 wherein the vinyl ester is vinyl stearate, said alkyl ester is isobornyl methacrylate or lauryl methacrylate and the crosslinking agent is divinylbenzene.

16. The method of claim 8 wherein the tertiary-alkylstyrene is tertiary-butylstyrene, said alkyl ester is lauryl methacrylate or stearyl methacrylate and the crosslinking agent is divinylbenzene.

17. The method of claim 8 wherein said tertiary-alkylstyrene is tertiary-butylstyrene and is a comonomer with 2-ethylhexyl acrylate and lauryl methacrylate and the crosslinking agent is divinylbenzene.

18. The method of claim 8 wherein said tertiary-alkylstyrene is tertiary-butylstryene and is a comonomer with 2-ethylhexyl acrylate and stearyl methacrylate and the crosslinking agent is divinylbenzene.

19. The method of claim 9 wherein the tertiary-alkylstyrene is tertiary-butylstyrene, said vinyl ester is vinyl stearate and the crosslinking agent is divinylbenzene.

* * * * *